United States Patent [19]

Gericke et al.

[11] Patent Number: 5,232,944
[45] Date of Patent: Aug. 3, 1993

[54] CHROMAN DERIVATIVES

[75] Inventors: Rolf Gericke, Seeheim; Manfred Baumgarth, Darmstadt; Ingeborg Lues, Darmstadt, all of Fed. Rep. of Germany; Jacques De Peyer, Bern, Switzerland; Rolf Bergmann, Reichelsheim, Fed. Rep. of Germany

[73] Assignee: Merck Patent Gesellschaft mit beschrankter Haftung, Darmstadt, Fed. Rep. of Germany

[21] Appl. No.: 870,749

[22] Filed: Apr. 20, 1992

Related U.S. Application Data

[63] Continuation of Ser. No. 593,405, Oct. 5, 1990, abandoned.

[30] Foreign Application Priority Data

Oct. 9, 1989 [DE] Fed. Rep. of Germany ....... 3933663

[51] Int. Cl.$^5$ ..................... A61K 31/35; C07D 311/22
[52] U.S. Cl. .................................. 514/456; 549/400; 549/401; 549/404; 549/399; 549/345; 549/60
[58] Field of Search .............. 549/404, 401, 400, 399, 549/345, 60; 514/456, 444

[56] References Cited

FOREIGN PATENT DOCUMENTS 2204868 11/1988 United Kingdom .

OTHER PUBLICATIONS

J. R. Weeks et al., "Routine Direct Measurement of Arterial Pressure in Unanesthetized Rats (25937)," Proc. Soc. Exp. Biol. Med. 104, 646–648 (1960).
R. Gericke et al., "3-Methyl-2H-1-benzopyran Potassium Channel Activators," Journal of Medicinal Chemistry, vol. 34, No. 10, 1991, 12 pp.

Primary Examiner—Nicky Chan
Attorney, Agent, or Firm—Millen, White, Zelano & Branigan

[57] ABSTRACT

Novel chroman derivatives of the formula I

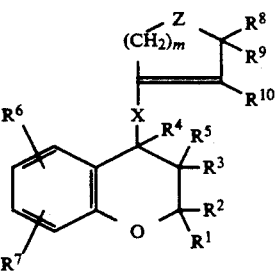

in which
X is O or $NR^{11}$,
Z is $CH_2$, O, S or CHHal,
$R^1$ and $R^5$ are each A,
$R^2$ is H or A,
$R^1$ and $R^2$ together are also alkylene having 3-6 C atoms,
$R^3$ is OH or OAc,
$R^4$ is H,
$R^3$ and $R^4$ together are also a bond,
$R^6$ and $R^7$ are each H, A, HO, AO, CHO, ACO, ACS, HOOC, AOOC, AO—CS, ACOO, A—C-S—O, hydroxyalkyl, $NO_2$, $NH_2$, NHA, $NA_2$, CN, F, Cl, Br, I, $CF_3$, ASO, $ASO_2$, AO—SO, AO—$SO_2$, AcNH, AO—CO—NH, $H_2$NSO, HANSO, $A_2$NSO, $H_2NSO_2$, $HANSO_2$, $A_2NSO_2$, $H_2$NCO, HANCO, $A_2$NCO, $H_2$NCS, HANCS, $A_2$NCS, ASONH, $ASO_2$NH, AOSONH, $AOSO_2$NH, ACO-alkyl, nitro-alkyl, cyanoalkyl, A—C(-=NOH) or A—C(=$NNH_2$),
$R^8$ and $R^9$ are each H or A or together are =O or =S,
$R^{10}$ is H, Hal, CHO or $CH_2OH$,
$R^{11}$ is H, A, Ac or $CH_2OH$,
m is 1, 2 or 3,
Hal is F, Cl, Br or I,
A is alkyl having 1-6 C atoms,
-alkyl is alkylene having 1-6 C atoms and
Ac is alkanoyl having 1-8 C atoms or aroyl having 7-11 C atoms, and their salts show effects on the cardiovascular system.

3 Claims, No Drawings

CHROMAN DERIVATIVES

This application is a continuation of application Ser. No. 07/593,405, filed Oct. 5, 1990, now abandoned.

SUMMARY OF THE INVENTION

The invention relates to novel chroman derivatives of the formula I

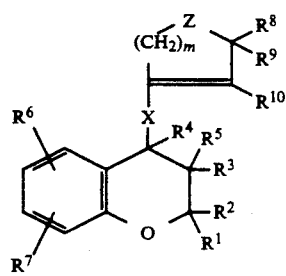

in which
X is O or $NR^{11}$,
Z is $CH_2$, O, S or CHHal,
$R^1$ and $R^5$ are each A,
$R^2$ is H or A,
$R^1$ and $R^2$ together are also alkylene having 3–6 C atoms,
$R^3$ is OH or OAc,
$R^4$ is H,
$R^3$ and $R^4$ together are also a bond,
$R^6$ and $R^7$ are each H, A, HO, AO, CHO, ACO, ACS, HOOC, AOOC, AO—CS, ACOO, A—C-S—O, hydroxyalkyl, $NO_2$, $NH_2$, NHA, $NA_2$, CN, F, Cl, Br, I, $CF_3$, ASO, $ASO_2$, AO—SO, AO—$SO_2$, AcNH, AO—CO—NH, $H_2NSO$, HANSO, $A_2NSO$, $H_2NSO_2$, $HANSO_2$, $A_2NSO_2$, $H_2NCO$, HANCO, $A_2NCO$, $H_2NCS$, HANCS, $A_2NCS$, ASONH, $ASO_2NH$, AOSONH, $AOSO_2NH$, ACO-alkyl, nitro-alkyl, cyanoalkyl, A—C(=NOH) or A—C(=$NNH_2$),
$R^8$ and $R^9$ are each H or A or together are =O or =S,
$R^{10}$ is H, Hal, CHO or $CH_2OH$,
$R^{11}$ is H, A, Ac or $CH_2OH$,
m is 1, 2 or 3,
Hal is F, Cl, Br or I,
A is alkyl having 1–6 C atoms,
alkyl is alkylene having 1–6 C atoms and
Ac is alkanoyl having 1–8 C atoms or aroyl having 7–11 C atoms,
and their salts.

Similar compounds are known from GB-A-2,204,868.

The invention was based on the object of finding novel compounds having useful properties, in particular those which can be used for the production of medicaments It has been found that the compounds of the formula I and their physiologically acceptable salts possess, combined with good tolerability, useful pharmacological properties. Thus, they show effects on the cardiovascular system, it usually being possible to observe a preferred effect on the coronary system and on the bronchial system at lower doses and an additional hypotensive effect at higher doses. In the coronary system, for example, decreases in resistance and increases in flow occur, the influence on the heart rate remaining low. Furthermore, the compounds show a relaxant effect on various smooth muscle organs (gastrointestinal tract, respiratory system and uterus). The effects of the compounds can be determined with the aid of methods which are known per se, such as are given, for example, in EP-A1-76,075, EP-A1-173,848 or AU-A-45,547/85 (Derwent Farmdoc No. 86081769) and by K. S. Meesmann et al., Arzneimittelforschung 25 (11), 1975, 1770–1776. Suitable experimental animals are, for example, mice, rats, guinea pigs, dogs, cats, apes or pigs.

The compounds can therefore be used as active medicament compounds in human and veterinary medicine. In addition, they can be used as intermediates for the preparation of further active medicament compounds.

In the formulae given, A is a preferably unbranched alkyl group having 1–6, preferably 1–4, in particular 1, 2 or 3 C atoms, in detail preferably methyl, in addition preferably ethyl, propyl, isopropyl, butyl, isobutyl, and furthermore preferably sec.-butyl, tert.-butyl, pentyl, isopentyl (3-methylbutyl), hexyl or isohexyl (4-methylpentyl).

If $R^1$ and $R^2$ together are alkylene, the alkylene group is preferably unbranched, in detail preferably —$(CH_2)_n$—, where n is 3, 4, 5 or 6.

The group "-alkyl" is preferably —$CH_2$— or —$CH_2CH_2$—.

Ac is preferably alkanoyl having 1–6, in particular 1, 2, 3 or 4 C atoms, in detail preferably formyl or acetyl, furthermore preferably propionyl, butyryl, isobutyryl, pentanoyl or hexanoyl, and in addition preferably benzoyl, o-, m- or p-toluyl, 1- or 2-naphthoyl.

X is preferably O, and in addition preferably NH.
Z is preferably $CH_2$, and in addition preferably O.
$R^1$ and $R^2$ are preferably each alkyl, in particular each methyl or ethyl, preferably each methyl.
If $R^4$ is H, $R^3$ is preferably OH, and in addition O—CHO or O—$COCH_3$.
$R^5$ is preferably methyl, and in addition ethyl.
In $R^6$ and $R^7$, the following are preferably:

| | |
|---|---|
| A: | methyl, and in addition ethyl; |
| AO: | methoxy, and in addition ethoxy; |
| ACO: | acetyl, and in addition propionyl; |
| ACS: | thioacetyl, and in addition thiopropionyl; |
| AOOC: | methoxycarbonyl, and in addition ethoxycarbonyl; |
| AO—CS: | methoxythiocarbonyl, and in addition ethoxythiocarbonyl; |
| ACOO: | acetoxy, and in addition propionoxy; |
| ACSO: | thio(no)acetoxy, and in addition thio(no)propionoxy; |
| hydroxyalkyl: | hydroxymethyl or 1- or 2-hydroxyethyl; |
| mercaptoalkyl: | mercaptomethyl or 1- or 2-mercaptoethyl; |
| NHA: | methylamino, and in addition ethylamino; |
| $NA_2$: | dimethylamino, and in addition diethylamino; |
| ASO: | methylsulfinyl, and in addition ethylsulfinyl; |
| $ASO_2$: | methylsulfonyl, and in addition ethylsulfonyl; |
| AO—SO: | methoxysulfinyl, and in addition ethoxysulfinyl; |
| AO—$SO_2$: | methoxysulfonyl, and in addition ethoxysulfonyl; |
| Ac—NH: | acetamido, and in addition formamido, propionamido or benzamido; |
| AO—CO—NH: | methoxycarbonylamino, and in addition ethoxycarbonylamino; |
| HANSO: | methylaminosulfinyl, and in addition ethylaminosulfinyl; |
| $A_2NSO$: | dimethylaminosulfinyl, and in addition diethylaminosulfinyl; |
| $HANSO_2$: | methylaminosulfonyl, and in addition ethylaminosulfonyl; |

| | |
|---|---|
| A$_2$NSO$_2$: | dimethylaminosulfonyl, and in addition diethylaminosulfonyl; |
| HANCO: | N-methylcarbamoyl, and in addition N-ethylcarbamoyl; |
| A$_2$NOC: | N,N-dimethylcarbamoyl, and in addition N,N-diethylcarbamoyl; |
| HANCS: | N-methylthiocarbamoyl, and in addition N-ethylthiocarbamoyl; |
| A$_2$NCS: | N,N-dimethylthiocarbamoyl, and in addition N,N-diethylthiocarbamoyl; |
| ASONH: | methylsulfinylamino, and in addition ethylsulfinylamino; |
| ASO$_2$NH: | methylsulfonylamino, and in addition ethylsulfonylamino; |
| AOSONH: | methoxysulfinylamino, and in addition ethoxysulfinylamino; |
| AOSO$_2$NH: | methoxysulfonylamino, and in addition ethoxysulfonylamino; |
| ACO-alkyl: | 2-oxopropyl, 2-oxobutyl, 3-oxobutyl, 3-oxopentyl; |
| Nitroalkyl: | nitromethyl, 1- or 2-nitroethyl; |
| Cyanoalkyl: | cyanomethyl, 1- or 2-cyanoethyl; |
| A—C(=NOH): | 1-oximinoethyl, and in addition 1-oximinopropyl; |
| A—C(=NNH$_2$): | 1-hydrazinoethyl, and in addition 1-hydrazinopropyl. |

The radicals $R^6$ and $R^7$ are preferably in the 6- and 7-position of the chroman system. However, they may also be in the 5- and 6-, 5- and 7-, 5- and 8-, 6- and 8- and 7- and 8-position.

One of the radicals $R^6$ and $R^7$ is preferably H, whereas the other is different from H. This other radical is preferably in the 6-position, but also in the 5-, 7- or 8-position, and is preferably CN or NO$_2$, in addition preferably CHO, ACO (in particular acetyl), AOOC (in particular methoxycarbonyl or ethoxycarbonyl), ACOO (in particular acetoxy), and furthermore preferably F, Cl, Br, I, CF$_3$, H$_2$NCO, H$_2$NCS or NH$_2$.

$R^8$ and $R^9$ together are preferably =O.

$R^{10}$ and $R^{11}$ are preferably each H.

$R^{11}$ is preferably H.

The parameter m is preferably 1, and in addition preferably 2.

Hal is preferably Cl or Br.

Accordingly, the invention in particular relates to those compounds of the formula I in which at least one of the radicals mentioned has one of the previously mentioned preferred meanings. Some preferred groups of compounds can be expressed by the formulae Ia to Ie below, which correspond to the formula I and in which the radicals not designated in more detail have the meaning given in the formula I, in which however in Ia $R^1$ and $R^2$ are each A;

in Ib $R^1$ and $R^2$ are each CH$_3$;

in Ic $R^1$ and $R^2$ together are alkylene having 3–6 C atoms;

in Id $R^5$ is CH$_3$;

in Ie $R^1$, $R^2$ and $R^5$ are each CH$_3$.

Compounds of the formulae I' and Ia' to Ie' are furthermore preferred which correspond to the formulae I and Ia to Ie, but in which in each case additionally $R^3$ is OH and $R^4$ is H.

Compounds of the formulae I'' and Ia'' to Ie'' are furthermore preferred which correspond to the formulae I and Ia to Ie, but in which in each case additionally X is O, Z is CH$_2$, m is 1, $R^8$ and $R^9$ together are =O and $R^{10}$ is H.

Compounds of the formulae I, I', I'', Ia to Ie, Ia' to Ie' and Ia'' to Ie'' are in addition preferred, in which in each case additionally (a) $R^6$ is different from H and $R^7$ is H;

(b) $R^6$ is different from H and is in the 6-position and $R^7$ is H;

(c) $R^6$ is NO$_2$, CN, CHO, ACO, HOOC, AOOC, ACOO, F, Cl, Br, I, CF$_3$, H$_2$NCO, H$_2$NCS or NH$_2$ and $R^7$ is H;

(d) $R^6$ is NO$_2$, CN, CHO, ACO, HOOC, AOOC, ACOO, F, Cl, Br, I, CF$_3$, H$_2$NCO, H$_2$NCS or NH$_2$ and is in the 6-position and $R^7$ is H;

(e) $R^6$ is NO$_2$, CN, CHO, CH$_3$CO, CH$_3$OOC, C$_2$H$_5$OOC or CH$_3$COO and $R^7$ is H;

(f) $R^6$ is NO$_2$, CN, CHO, CH$_3$CO, CH$_3$OOC, C$_2$H$_5$OOC or CH$_3$COO and is in the 6-position and $R^7$ is H;

(g) $R^6$ is NO$_2$ or CN and $R^7$ is H;

(h) $R^6$ is NO$_2$ or CN and is in the 6-position and $R^7$ is H;

(i) $R^6$ is CN and $R^7$ is H;

(j) $R^6$ is CN and is in the 6-position and $R^7$ is H.

Otherwise, the radicals and parameters X, Z, $R^1$ to $R^{11}$, m, Hal, A, "-alkyl" and Ac above and below have the meanings given in formula I, if not expressly stated otherwise.

The invention in addition relates to a process for the preparation of chroman derivatives of the formula I, characterized in that a 3,4-epoxychroman of the formula II

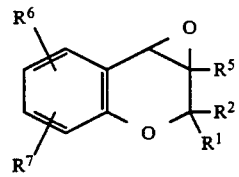

in which $R^1$, $R^2$, $R^5$, $R^6$ and $R^7$ have the meanings given in formula I is reacted with a compound of the formula III

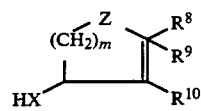

in which X, Z, $R^8$, $R^9$, $R^{10}$ and m have the meanings given in formula I, or with one of its reactive derivatives and/or in that a compound of the formula I, in which $R^3$ is OH and $R^4$ is H, is dehydrated and/or in that one or more of the radicals X, Z, $R^3$, $R^6$ and/or $R^7$ are converted into other radicals X, Z, $R^3$, $R^6$ and/or $R^7$ in a compound of the formula I and/or in that a basic compound of the formula I is converted into one of its acid addition salts by treating with an acid.

The compounds of the formula I are otherwise prepared by methods which are known per se, as are described in the literature (for example in the standard works such as Houben-Weyl, Methoden der organischen Chemie (Methods of Organic Chemistry), Georg-Thieme Verlag, Stuttgart; Organic Reactions, John Wiley & Sons, Inc., New York; and in the abovementioned patent applications), in particular under reaction conditions which are known and suitable for the reactions mentioned. In this case, use can also be made of variants which are known per se but which are not mentioned in more detail here.

The starting materials may also be formed, if desired, in situ in such a way that they are not isolated from the reaction mixture, but immediately reacted further to give the compounds of the formula I.

Preferably, the compounds of the formula I are prepared by reacting compounds of the formula II with compounds of the formula III, preferably in the presence of an inert solvent at temperatures between about 0° and 150°, preferably 15° and 30°.

The starting materials II and III are usually known. If they are not known, they can be prepared by methods which are known per se. The starting materials of the formula II are obtainable by reacting 2-hydroxyacetophenones of the formula $2-HO-R^6R^7C_6H_2-COCH_3$ with ketones of the formula $R^1-CO-H^2$ to give corresponding 4-chromanones of the formula IVa

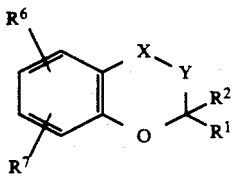

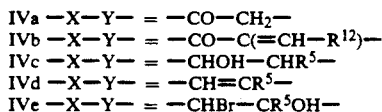

IVa $-X-Y- = -CO-CH_2-$
IVb $-X-Y- = -CO-C(=CH-R^{12})-$
IVc $-X-Y- = -CHOH-CHR^5-$
IVd $-X-Y- = -CH=CR^5-$
IVe $-X-Y- = -CHBr-CR^5OH-$ condensing with aldehydes of the formula $R^{12}-CHO$ ($R^{12}$=alkyl having 1-5 C atoms) to give 3-alkylidene-4-chromanones of the formula IVb, reducing, for example with NaBH$_4$, to give 3-alkyl-4-chromanols of the formula IVc, dehydrating, for example with p-toluenesulfonic acid, to give chromenes of the formula IVd and oxidizing, for example with 3-chloroperbenzoic acid. The last-mentioned oxidation can also be carried out in a number of steps. Thus, for example, the bromohydrins of the formula IVe can initially be prepared using N-bromosuccinimide in aqueous solution and these can subsequently be treated with a base, for example sodium hydroxide solution.

The chromenes of the formula IVd can also be obtained by condensation of salicylaldehydes of the formula $2-HO-R^6R^7C_6H^2-CHO$ with ketones of the formula $R^1-CO-CH_2-R^5$ to give hydroxyketones of the formula $2-HO-R^6R^7C_6H_2-CH=C-R^5-CO-R^1$, reaction with organolithium compounds of the formula $R^2-Li$ and subsequent hydrolysis to give diols of the formula $2-HO-R^6R^7C_6H_2-CH=CR^5-CR^1R^2-OH$, and cyclization with elimination of water.

Reactive derivatives of III which are suitable are the corresponding salts, for example the Na or K salts, which can also be formed in situ.

It is preferable to work in the presence of a base. Suitable bases are, for example, hydroxides, hydrides and also amides of alkali metals or alkaline earth metals, such as NaOH, KOH, Ca(OH)$_2$, NaH, KH, CaH$_2$, NaNl$_2$, KNH$_2$, and in addition organic bases such as triethylamine or pyridine, which can also be used in excess and then at the same time serve as solvent. In addition, it is often preferable to add catalytic or stoichiometric amounts of Cu$_2$Br$_2$, MgBr$_2$, titanium alkoxides or Lewis acids such as BF$_3$ etherate.

Suitable inert solvents are, in particular, alcohols such as methanol, ethanol, isopropanol, n-butanol or tert.-butanol; ethers such as diethyl ether, diisopropyl ether, tetrahydrofuran (THF) or dioxane; glycol ethers such as ethylene glycol monomethyl ether or ethylene glycol monoethyl ether (methyl glycol or ethyl glycol), ethylene glycol dimethyl ether (diglyme); ketones such as acetone or butanone; nitriles such as acetonitrile; nitro compounds such as nitromethane or nitrobenzene; esters such as ethyl acetate; amides such as dimethylformamide (DMF), dimethylacetamide or hexamethylphosphoramide; sulfoxides such as dimethyl sulfoxide (DMSO); chlorinated hydrocarbons such as dichloromethane, chloroform, trichloroethylene, 1,2-dichloroethane or carbon tetrachloride; hydrocarbons such as benzene, toluene or xylene. Mixtures of these solvents with one another are furthermore suitable.

The epoxide II can also be prepared in situ, for example by the action of a base on the corresponding bromohydrin IVe.

A compound of the formula I in which $R^3$=OH and $R^4$=H can be converted into a compound of the formula I in which $R^3$ and $R^4$ together are a bond by treating with a dehydrating agent. This is carried out, for example by the action of one of the bases mentioned, for example NaOH, KOH or NaH, in one of the solvents mentioned, for example tetrahydrofuran, dioxane or DMSO, at temperatures between 0° and 150°.

Furthermore, one or more of the radicals X, Z, $R^3$, $R^6$ and/or $R^7$ can be converted into other radicals X, Z, $R^3$, $R^6$ and/or $R^7$ in a compound of the formula I.

For example, it is possible to replace an H atom by a halogen atom by means of a halogenation or by a nitro group by means of a nitration and/or to reduce a nitro group to an amino group and/or to alkylate or acylate an amino or hydroxyl group and/or to convert a cyano group (for example with HCl in water/methanol at 20°-100°) into a carboxyl group or (for example with Raney nickel in water/acetic acid/pyridine in the presence of sodium phosphate) into a formyl group or (for example with KOH in tert.-butanol) into a carbamoyl group or (for example with H$_2$S in pyridine/triethylamine) into a thiocarbamoyl group.

Nitration is carried out under customary conditions, for example using a mixture of concentrated HNO$_3$ and concentrated H$_2$SO$_4$ at temperatures between 0° and 30°.

Halogenation can be carried out, for example, using elemental chlorine or bromine in one of the customary inert solvents at temperatures between about 0° and 30°.

A primary or secondary amino group and/or an OH group can be converted into the corresponding secondary or tertiary amino group and/or alkoxy group by treating with alkylating agents. Suitable alkylating agents are, for example, compounds of the formulae A—Cl, A—Br or A—I or corresponding sulfuric acid or sulfonic acid esters, such as methyl chloride, bromide or iodide, dimethyl sulfate or methyl p-toluenesulfonate. In addition, for example, one or two methyl groups can be introduced with formaldehyde in the presence of formic acid. The alkylation is preferably carried out in the presence or absence of one of the inert solvents mentioned, for example DMF, at temperatures between about 0° and about 120°, in which case a catalyst can also be present, preferably a base such as potassium tert.-butoxide or NaH.

Suitable acylating agents for the acylation of amino or hydroxyl groups are preferably the halides (for example chlorides or bromides) or anhydrides of carboxylic acids of the formula Ac—OH, for example acetic anhydride, propionyl chloride, isobutyryl bromide, formic acid/acetic anhydride and benzoyl chloride. The addition of a base such as pyridine or triethylamine during the acylation is possible. The acylation is preferably carried out in the presence or absence of an .inert solvent, for example a hydrocarbon such as toluene, a nitrile such as acetonitrile, an amide such as DMF or an excess of a tertiary base such as pyridine or triethylamine, at temperatures between about 0° and about 160°, preferably between 20° and 120°. Formylation is also carried out using formic acid in the presence of pyridine.

A base of the formula I can be converted into the respective acid addition salt using an acid. Acids which give physiologically acceptable salts are particularly suitable for this reaction. Thus, inorganic acids can be used, for example sulfuric acid, nitric acid, hydrohalic acids such as hydrochloric acid or hydrobromic acid, phosphoric acids such as orthophosphoric acid, sulfamic acid, and in addition organic acids, in particular aliphatic, alicyclic, araliphatic, aromatic or heterocyclic monobasic or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2- or 3-phenylpropionic acid, citric acid, gluconic acid, ascorbic acid, nicotinic acid, isonicotinic acid, methanesulfonic or ethanesulfonic acid, ethanedisulfonic acid, 2-hydroxyethanesulfonic acid, benzenesulfonic acid, p-toluenesulfonic acid, naphthalenemonosulfonic and -disulfonic acids, and laurylsulfuric acid. Salts with physiologically unacceptable acids, for example picrates, can be used for purifying the compounds of the formula I.

The compounds of the formula I may possess one or more chiral centers. They can therefore be obtained during their preparation as racemates or also, if optically active starting materials are used, in optically active form. If the compounds have two or more chiral centers, they may be obtained during synthesis as mixtures of racemates from which the individual racemates can be isolated in pure form, for example by recrystallizing from inert solvents. Thus, for example, compounds of the formula I in which $R^1 = R^2$, $R^3 = OH$ and $R^4 = H$ have two chiral centers; during preparation by reaction of II with III, however, very predominantly only one racemate having the trans-position of the substituents $R^3 = OH$ and $R^5$ is formed. Racemates obtained can, if desired, be separated mechanically or chemically into their enantiomers by methods known per se. Thus, diastereomers can be formed from the racemate by reaction with an optically active resolving agent. Suitable resolving agents for basic compounds of the formula I are, for example, optically active acids, such as the D-and L-forms of tartaric acid, dibenzoyltartaric acid, diacetyltartaric acid, camphorsulfonic acids, mandelic acid, malic acid or lactic acid. Carbinols (I, $R^3 = OH$) can in addition be esterified and then resolved with the aid of chiral acylating reagents, for example D- or L-α-methylbenzyl isocyanate (cf. EP-A1-120,428). The different forms of the diastereomers can be separated in a manner known per se, for example by fractional crystallization, and the enantiomers of the formula I can be liberated in a manner known per se from the diastereomers Resolution of enantiomers is in addition carried out by chromatography on optically active support materials.

The compounds of the formula I and their physiologically acceptable salts can be used for the production of pharmaceutical preparations, in particular in nonchemical ways. In this connection, they can be brought into a suitable form for administration together with at least one solid, liquid and/or semi-liquid excipient or auxiliary and, if desired, in combination with one or more further active compound(s).

The invention in addition relates to agents, in particular pharmaceutical preparations, containing at least one compound of the formula I and/or one of its physiologically acceptable salts.

These preparations can be used as medicaments in human or veterinary medicine. Suitable excipients are organic or inorganic substances which are suitable for enteral (for example oral), parenteral or topical administration and which do not react with the novel compounds, for example water, vegetable oils, benzyl alcohols, polyethylene glycols, glycerol triacetate, gelatin, carbohydrates such as lactose or starch, magnesium stearate, talc or petroleum jelly. In particular, tablets, coated tablets, capsules, syrups, elixirs or drops are used for oral administration, suppositories are used for rectal administration, solutions, preferably oily or aqueous solutions, and in addition suspensions, emulsions or implants are used for parenteral administration, and ointments, creams or powders are used for topical application. The novel compounds can also be lyophilized and the lyophilizates obtained used, for example, for the production of injection preparations. The preparations mentioned can be sterilized and/or can contain auxiliaries such as lubricants, preservatives, stabilizers and/or wetting agents, emulsifiers, salts for influencing the osmotic pressure, buffer substances, colorants and flavorings and/or aromatizers. They can, if desired, also contain one or more further active compounds, for example one or more vitamins.

The compounds of the formula I and their physiologically acceptable salts can be administered to humans or animals, in particular mammals such as apes, dogs, cats, rats or mice and can be used in the therapeutic treatment of the human or animal body and also in the control of diseases, in particular in the therapy and/or prophylaxis of disturbances of the cardiovascular system, in particular decompensated cardiac insufficiency, angina pectoris, peripheral or cerebral vascular disorders, and disease conditions which are connected with high blood pressure, and in addition disorders which are connected with changes in the non-vascular musculature, for example asthma or urinary incontinence.

In this connection, the substances according to the invention are usually administered analogously to known antianginals or hypotensives, for example nicorandil or cromakalim, preferably in doses between about 0.01 and 5 mg, in particular between 0.02 and 0.5 mg per dose unit. The daily dose is preferably between about 0.0001 and 0.1, in particular between 0.0003 and 0.01 mg/kg of body weight. The specific dose for each particular patient depends, however, on a variety of factors, for example on the efficacy of the specific compound employed, on the age, body weight, the general state of health, sex, on the food, on the time and route of administration, on the excretion rate, medicament combination and severity of the particular disease to which the therapy applies. Adjustment of the dosage based on these factors is routine experimentation for one of ordinary skill in the art.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, if any, cited above and below, and of corresponding application Federal Republic of Germany P 39 33 663.8, filed Oct. 9, 1989, are hereby incorporated by reference.

In the following examples, "customary working up" means:

water is added, if necessary, the mixture is extracted using an organic solvent such as ethyl acetate, the organic phase is separated off, dried over sodium sulfate, filtered and evaporated, and the residue is purified by chromatography and/or crystallization.

EXAMPLES

EXAMPLE 1

2.1 g of 1,3-cyclopentanedione are dissolved in 200 ml of THF under $N_2$, 650 mg of NaH (80% in mineral oil) are added, the mixture is stirred for 1 hour, a solution of 4.6 g of 2,2,3-trimethyl-3,4-epoxy-6-cyanochroman ("IIa") in 20 ml of THF, then 2.4 ml of $BF_3$ etherate are added successively and the mixture is stirred overnight at 20°. The mixture is evaporated and the 2,2,3-trimethyl-4-(3-oxo-1-cyclopenten-1-yloxy)-6-cyano-3-chromanol ("A") obtained is purified by chromatography on silica gel (ethyl acetate/methanol 100:1); m.p. 204°-206° (from isopropanol).

2,2,3-trimethyl-4-(3-oxo-1-cyclohexen-1-yloxy)-6-cyano-3-chromanol is obtained analogously using 1,3-cyclohexanedione.

2,2,3-trimethyl-4-(3-oxo-1-cyclopenten-1-yloxy)-3-chromanol 2,2,3-trimethyl-4-(3-oxo-1-cyclopenten-1-yloxy)-6-chloro-3-chromanol 2,2,3-trimethyl-4-(3-oxo-1-cyclopenten-1-yloxy)-6-bromo-3-chromanol 2,2,3-trimethyl-4-(3-oxo-1-cyclopenten-1-yloxy)-6-acetyl-3-chromanol 2,2,3-trimethyl-4-(3-oxo-1-cyclopenten-1-yloxy)-6-methoxycarbonyl-3-chromanol 2,2,3-trimethyl-4-(3-oxo-1-cyclopenten-1-yloxy)-6-ethoxycarbonyl-3-chromanol 2,2,3-trimethyl-4-(3-oxo-1-cyclopenten-1-yloxy)-6-nitro-3-chromanol 2,2,3-trimethyl-4-(3-oxo-1-cyclopenten-1-yloxy)-6-acetamido-3-chromanol 2,2,3-trimethyl-4-(3-oxo-1-cyclopenten-1-yloxy)-7-acetamido-3-chromanol 2,2,3-trimethyl-4-(3-oxo-1-cyclopenten-1-yloxy)-6-acetamido-7-nitro-3-chromanol 2,2-diethyl-3-methyl-(3-oxo-1-cyclopenten-1-yloxy)-6-cyano-3-chromanol 2,2-tetramethylene-3-methyl-(3-oxo-1-cyclopenten-1-yloxy)-6-cyano-3-chromanol 2,2-pentamethylene-3-methyl-(3-oxo-1-cyclopenten-1-yloxy)-6-cyano-3-chromanol are obtained analogously from:

2,2,3-trimethyl-3,4-epoxy-chroman
2,2,3-trimethyl-3,4-epoxy-6-chloro-chroman
2,2,3-trimethyl-3,4-epoxy-6-bromo-chroman
2,2,3-trimethyl-3,4-epoxy-6-acetyl-chroman
2,2,3-trimethyl-3,4-epoxy-6-methoxycarbonyl-chroman
2,2,3-trimethyl-3,4-epoxy-6-ethoxycarbonyl-chroman
2,2,3-trimethyl-3,4-epoxy-6-nitro-chroman
2,2,3-trimethyl-3,4-epoxy-6-acetamido-chroman
2,2,3-trimethyl-3,4-epoxy-6-acetamido-chroman
2,2,3-trimethyl-3,4-epoxy-6-acetamido-7-nitro-chroman
2,2-diethyl-3-methyl-3,4-epoxy-6-cyano-chroman
2,2-tetramethylene-3-methyl-3,4-epoxy-6-cyano-chroman
2,2-pentamethylene-3-methyl-3,4-epoxy-6-cyano-chroman using 1,3-cyclopentanedione

EXAMPLE 2

(3S,4R)-2,2,3-Trimethyl-4-(3-oxo-1-cyclopenten-1-yloxy)-6-cyano-3-chromanol is obtained analogously to Example 1 from (−)-(3S,4S)-2,2,3-trimethyl-3,4-epoxy-6-cyano-chroman ["(−)-IIa"] and 1,3-cyclopentanedione.

(3R,4S)-2,2,3-Trimethyl-4-(3-oxo-1-cyclopenten-1-yloxy)-6-cyano-3-chromanol is obtained analogously from (+)-(3R,4R)-2,2,3-trimethyl-3,4-epoxy-6-cyano-chroman.

EXAMPLE 3

2.15 g of IIa are dissolved in 30 ml of DMSO under $N_2$, 0.2 g of NaH is first added with stirring, then 1.5 g of 3-amino-2-cyclopenten-1-one are added in portions and the mixture is stirred for 24 hours at 20°. Customary working up gives 2,2,3-trimethyl-4-(3-oxo-1-cyclopenten-1-ylamino)-6-cyano-3-chromanol ("B").

2,2,3-Trimethyl-4-[2-oxofuran-4(5H)-ylamino]-6-cyano-3-chromanol is obtained analogously from IIa and 4-amino-2(5H)-furanone.

2,2,3-Trimethyl-4-[N-methyl-N-(3-oxo-1-cyclopenten-1-yl)-amino]-6cyano-3-chromanol is obtained analogously from IIa and 3-methylamino-2-cyclopenten-1-one.

2,2,3-trimethyl-4-[N-methyl-N-(2-oxofuran-4(5H)-yl)-amino]-6-cyano-3-chromanol is obtained analogously from IIa and 4-methylamino-2(5H)-furanone.

2,2,3-Trimethyl-4-[N-methyl-N-(1-methyl-2-oxopyrrol-4(5H)-yl)-amino]-6-cyano-3-chromanol is obtained analogously from IIa and 1-methyl-4-methylamino-2(5H)-pyrrolone.

The following are obtained analogously from the corresponding 3,4-epoxychromones:

2,2,3-trimethyl-4-(3-oxo-1-cyclopenten-1-yl-amino)-3-chromanol 2,2,3-trimethyl-4-(3-oxo-1-cyclopenten-1-yl-amino)-6-chloro-3-chromanol 2,2,3-trimethyl-4-(3-oxo-1-cyclopenten-1-yl-amino)-6-bromo-3-chromanol 2,2,3-trimethyl-4-(3-oxo-1-cyclopenten-1-yl-amino)-6-methoxycarbonyl-3-chromanol 2,2,3-trimethyl-4-(3-oxo-1-cyclopenten-1-yl-amino)-6-ethoxycarbonyl-3-chromanol 2,2,3-trimethyl-4-(3-oxo-1-cyclopenten-1-yl-amino)-6-nitro-3-chromanol

EXAMPLE 4

2,2,3-Trimethyl-4-[2-oxofuran-4(5H)-yloxy]-6-cyano-3-chromanol is obtained analogously to Example 1 from IIa and tetronic acid.

2,2,3-Trimethyl-4-[2-oxothiophen-4(5H)-yloxy]-6-cyano-3-chromanol is obtained analogously from IIa and thiotetronic acid.

EXAMPLE 5

A mixture of 3.12 g of "B", 20 g of formic-acetic anhydride and 50 ml of THF is stirred under $N_2$ for 7 hours. The mixture is evaporated, worked up in the customary manner and 2,2,3-trimethyl-4-[N-formyl-N-(3-oxo-1-cyclopenten-1-yl)-amino]-6-cyano-3-chromanol is obtained.

EXAMPLE 6

A solution of 3.12 g of "B" in 150 ml of acetone is mixed three times every hour with 2.5 ml of 37% aqueous formaldehyde solution and stirred at pH 8–9 (addition of sodium hydroxide solution) for a total of hours. Customary working up gives 2,2,3-trimethyl-4-(2-hydroxymethyl-3-oxo-1-cyclopenten-1-ylamino)-6-cyano-3-chromanol.

EXAMPLE 7

1.4 g of the product obtained according to Example 6 are oxidized using 2.2 g of Collin's reagent in 250 ml of dichloromethane for 10 minutes, worked up as customary (chromatography on silica gel; dichloromethane/methanol 97:3) and 2,2,3-trimethyl-4-(2-formyl-3-oxo-1-cyclopenten-1-ylamino)-6-cyano-3-chromanol is obtained.

EXAMPLE 8

A solution of 1.1 g of "B" in a mixture of 35 ml of dichloromethane and 35 ml of dioxane is mixed with 700 mg of xenon difluoride, stirred at 20° for 5 hours and poured into water. Customary working up gives 2,2,3-trimethyl-4-(2-fluoro-3-oxo-1-cyclopenten-1-ylamino)-6-cyano-3-chromanol.

EXAMPLE 9

A solution of 156 mg of "B" in a mixture of 5 ml of dichloromethane and 5 ml of dioxane is stirred at 20° for 1 hour with 77 mg of N-chlorosuccinimide and worked up in the customary manner. 2,2,3-Trimethyl-4-(2-chloro-3-oxo-1-cyclopenten-1-ylamino)-6-cyano-3-chromanol is obtained.

2,2,3-Trimethyl-4-(2-bromo-3-oxo-1-cyclopenten-1-ylamino)-6-cyano-3-chromanol is obtained analogously using N-bromosuccinimide.

EXAMPLE 10

A mixture of 2 g of "A", 11.7 ml of formic acid and 3.3 ml of acetic anhydride is allowed to stand at 20° for 16 hours and is subsequently warmed to 40°–45° for 2 hours. Evaporation and customary working up gives 2,2,3-trimethyl-3-formyloxy-4-(3-oxo-1-cyclopenten-1-yloxy)-6-cyano-chroman.

EXAMPLE 11

A mixture of 1 g of "A" and 5 ml of acetic anhydride is boiled for 1 hour. The mixture is cooled, worked up in a customary manner and gives 2,2,3-trimethyl-3-acetoxy-4-(3-oxo-1-cyclopenten-1-yloxy)-6-cyano-chroman.

EXAMPLE 12

A solution of 3.46 g of 2,2,3-trimethyl-4-(3-oxo-1-cyclopenten-1-yloxy)-6-methoxycarbonyl-3-chromanol in 100 ml of 33% ethanolic dimethylamine solution is heated to 100° in an autoclave for 10 days. The mixture is cooled, worked up in a customary manner and gives 2,2,3-trimethyl-4-(3-oxo-1-cyclopenten-1-yloxy)-6-dimethylaminocarbonyl-3-chromanol.

EXAMPLE 13

HCl is passed into a boiling solution of 1 g of "A" in 50 ml of methanol and 2 ml of water with stirring for 14 hours. The mixture is allowed to cool, worked up in a customary manner and gives 2,2,3-trimethyl-4-(3-oxo-1-cyclopenten-1-yloxy)-6-carboxy-3-chromanol.

EXAMPLE 14

A mixture of 3.13 g of "A", 31 g of $Na_3PO_4 \cdot 12H_2O$, 28 ml of pyridine, 28 ml of water, 67 ml of acetic acid and 25 g of Raney Ni (water-moist) is stirred at 20° for 3 hours. After filtration, the mixture is worked up in a customary manner and gives 2,2,3-trimethyl-4-(3-oxo-1-cyclopenten-1-yloxy)-6-formyl-3-chromanol.

EXAMPLE 15

3.13 g of "A" are dissolved in 45 ml of tert.-butanol and 5 g of powdered KOH are added with stirring. Boiling for 1 hour and customary working up gives 2,2,3-trimethyl-4-(3-oxo-1-cyclopenten-1-yloxy)-6-carbamoyl-3-chromanol.

EXAMPLE 16

$H_2S$ is passed into a solution of 3.13 g of "A" in a mixture of 20 ml of pyridine and 10 ml of triethylamine at 20° for 5 hours, and the mixture is evaporated, worked up in a customary manner and gives 2,2,3-trimethyl-4-(3-oxo-1-cyclopenten-1-yloxy)-6-thiocarbamoyl-3-chromanol.

The examples below relate to pharmaceutical preparations which contain compounds of the formula I or their physiologically acceptable salts:

EXAMPLE A TABLETS

A mixture of 0.2 kg of "A", 136.3 kg of calcium hydrogenphosphate, 15 kg of cornflour, 10 kg of microcrystalline cellulose, 5.5 kg of insoluble polyvinylpyrrolidone (PVP), 1.5 kg of highly disperse $SiO_2$ and 1.5 kg of magnesium stearate is compressed in a customary manner to give tablets. Each 170 mg tablet contains 0.2 mg of active compound.

EXAMPLE B COATED TABLETS

Tablets are pressed analogously to Example A, but without adding PVP, and are subsequently coated in a customary manner with a coating of sucrose, potato starch, talc, tragacanth and colorant.

EXAMPLE C CAPSULES

Granules are prepared from 10 g of "A", 27.5 kg of lactose, 0.35 kg of hydroxypropylmethylcellulose and 0.7 kg of cornflour, these are mixed with 0.15 kg of highly disperse $SiO_2$ and 0.3 kg of magnesium stearate and the mixture is poured into hard gelatine capsules in a customary manner so that each capsule contains 0.1 mg of active compound.

EXAMPLE D LACQUERED TABLETS

Tablet cores (170 mg) are pressed from 0.2 kg of "A", 151.3 kg of lactose, 10 kg of microcrystalline cellulose, 5.5 kg of PVP, 1.5 kg of highly disperse $SiO_2$ and 1.5 kg of magnesium stearate, and are then lacquered in a customary manner so that each lacquered tablet is coated with 3.922 mg of a lacquer which consists of 2.2 mg of hydroxypropylmethylcellulose, 0.53 mg of polyethylene glycol 400, 0.85 mg of $TiO_2$, 0.122 mg of $Fe_2O_3$ and 0.22 mg of silicone oil.

EXAMPLE E AMPOULES

A solution of 10 g of "A" in 70 l of 1,2-propanediol is made up to 100 l with double-distilled water, sterile-filtered and poured into 1 ml ampoules which are then closed under sterile conditions. Each ampoule contains 0.1 mg of active compound Tablets, coated tablets, capsules, lacquered tablets or ampoules, which contain one or more of the other active compounds of the formula I and/or their physiologically acceptable salts, are obtainable analogously.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. 2,2,3-trimethyl-4-(3-oxo-1-cyclopenten-1-yloxy)-6-cyano-3-chromanol.
2. A pharmaceutical composition comprising a compound of claim 1 and a pharmaceutically acceptable carrier.
3. A method for the treatment of high blood pressure, comprising administering an effective amount of a compound of claim 1.

* * * * *